US008980564B2

(12) United States Patent
Goping et al.

(10) Patent No.: US 8,980,564 B2
(45) Date of Patent: Mar. 17, 2015

(54) PREDICTIVE MARKERS FOR TAXANE RESPONSIVENESS AND METHODS OF USE THEREOF

(75) Inventors: Ing Swie Goping, Edmonton (CA); John R. Mackey, Edmonton (CA); D. Alan Underhill, Edmonton (CA)

(73) Assignees: The Governors of the University of Alberta, Edmonton (CA); Alberta Health Services, Edmonton (CA)

( * ) Notice: Subject to any disclaimer, the term of this patent is extended or adjusted under 35 U.S.C. 154(b) by 0 days.

(21) Appl. No.: 13/510,799

(22) PCT Filed: Nov. 19, 2010

(86) PCT No.: PCT/CA2010/001830
§ 371 (c)(1),
(2), (4) Date: Sep. 21, 2012

(87) PCT Pub. No.: WO2011/060537
PCT Pub. Date: May 26, 2011

(65) Prior Publication Data
US 2013/0178515 A1  Jul. 11, 2013

Related U.S. Application Data

(60) Provisional application No. 61/263,174, filed on Nov. 20, 2009.

(51) Int. Cl.
*G01N 33/53* (2006.01)
*G01N 33/68* (2006.01)
*A61K 31/337* (2006.01)
*G01N 33/574* (2006.01)

(52) U.S. Cl.
CPC .......... *G01N 33/6893* (2013.01); *A61K 31/337* (2013.01); *G01N 33/57415* (2013.01); *G01N 33/57496* (2013.01); *G01N 2333/4703* (2013.01); *G01N 2800/52* (2013.01)
USPC ........................................................ 435/7.1

(58) Field of Classification Search
CPC .................................................... A61K 39/00
See application file for complete search history.

(56) References Cited

FOREIGN PATENT DOCUMENTS

| EP | 10 83 0993 | 2/2013 |
| WO | WO2004/111603 | 12/2004 |
| WO | WO 2004/111603 A2 * | 12/2004 |
| WO | WO2009/140304 | 11/2009 |

OTHER PUBLICATIONS

Kitada et al (American Journal of Pathology, 152(1): 51-61).*
Strobel et al (Oncogene, 1998, 17: 2419-2427).*
Invitrogen Manual for RiboGreen® fluorescence method, 2008.*
Kitada et al (American Journal of Phathology, 152(1): 51-61).*
O'Brien et al (Annals of Oncology, 1999, 10: 205-210).*
Cannings et al (Breast Cancer Res Treat, 2007, 102(2): 173-179).*
Kitada et al (American Journal of Pathology, 1998, 152(1): 51-61).*
Peng et al (Neurosci Lett, 1981, 21(3): Abstract).*
International Search Report and Written Opinion issued in PCT/CA2010/001830 on Feb. 25, 2011.
Bonnefoi et al., Predictive signatures for chemotherapy sensitivity in breast cancer: Are they ready for use in the clinic? Eur J Cancer Jul. 2009;45(10)1733-1743.
The International Preliminary Report on Patentability dated May 31, 2012 issued in PCT/CA2010/001830.
Craik et al., The BH3-only protein Bad confers breast cancer taxane sensitivity through a nonapoptotic mechanism. Oncogene Sep. 30, 2010:29(39):5381-5391.
Luo et al., Relationship of the expression of bcl-2 and bad in breast cancer cell with chemosensitivity, (Journal for Chongqing Medical University) Chongqing Yike Daxue Xuebao 2009;34(12):1651-1654 Accession No. 2010:431157 CAPLUS (abstract only).
McGrogan et al., Taxanes, microtubules and chemoresistant breast cancer. Biochim Biophys Acta, Apr. 2008;1785 (2):96-132.
Sinicrope et al., Proapoptotic Bad and Bid Protein Expression Predict Survival in Stages II and III Colon Cancers. Clin Cancer Res Jul. 1, 2008;14(13):4128-4133.
Strobel et al., BAD partly reverses paplitaxel resistance in human ovarian cancer cells. Oncogene Nov. 12, 1998;17(19):2419-2427.
Yu et al., Expression of the apoptosis-related genes BCL-2 and BAD in human breast carcinoma and their associated relationship with chemosensitivity. J Exp Clin Caner Res Aug. 7, 2010;29:107 ( 7 pages).
Borrell—"How accurate are cancer cell lines?", Nature, vol. 463, p. 858, Feb. 18, 2010.
Burdall et al. "Breast cancer cell lines: friend or foe?", Breast Cancer Res 2003, 5:89-95.
The Cancer Genome Atlas Research Network "Integrated genomic analyses of ovarian carcinoma", Nature, 474 (7353): 609-615, 2011.
Curtis et al. "The genomic and transcriptomic architecture of 2,000 breast tumours reveals novel subgroups", Nature, 486 (7403): 346-352, 2012.
Domcke et al. "Evaluating cell lines as tumour models by comparison of genomic profiles", Nature Communications, 4:2126, 2013.

(Continued)

*Primary Examiner* — Sean Aeder
(74) *Attorney, Agent, or Firm* — Goudreau Gage Dubuc; S. Serge Shahinian

(57) ABSTRACT

Taxanes are widely used in the treatment of breast cancer, although there are currently no validated predictive markers for taxane responsiveness. While the mechanism by which taxanes induce mitotic arrest is well documented, the signaling pathway that links mitotic arrest to cell death, is ill-defined. As described herein, the BH3-only protein Bad and Bik are prognostic indicators for overall survival after adjuvant taxane chemotherapy and a predictive marker for taxane responsiveness.

7 Claims, 10 Drawing Sheets

(56) References Cited

OTHER PUBLICATIONS

EBCTCG, "Comparisons between different polychemotherapy regimens for early breast cancer: meta-analyses of long-term . . . ", Lancet, vol. 379. pp. 432-444, Feb. 4, 2012.

Howell et al. "Overview of the impact of conventional systemic therapies on breast cancer", Endocrine-Related Cancer (2005), 12 S9-S16.

Masters—"Human cancer cell lines: fact and fantasy", Nature Reviews, Molecular Cell Biology, vol. 1, p. 233, Dec. 2000.

Monni et al. "PI3K/Akt pathway interference leads to specific gene expression alterations in breast cancer", Proc. Amer Assoc. Cancer Res, vol. 47, 2006.

Tudor et al. "Susceptibility to drug-induced apoptosis correlates with differential modulation of Bad, Bcl-2 and Bcl-xl protein levels", Cell Death and Differentiation (2000) 7, 574-586.

Veronesi et al. "Breast cancer", Lancet, vol. 265, pp. 1727-1741, May 14, 2005.

Boca et al., Testing multiple biological mediators simultaneously, Systems biology, vol. 30, No. 2, 2014, pp. 214-220.

Chan, Eric, Intergrating transcriptomics and proteomics, Highbeam Research, Apr. 1, 2006.

Chen et al., Discordant protein and mRNA expression in lung adenocarcinomas, Molecular & Cellular, 2002, 304-313.

Estevez et al., Weekly docetaxel as neoadjuvant chemotherapy for stage II and III breast cancer: efficay and correlation with biological markers in a phase II, multicenter study, Clinical Cancer Research, vol. 9, 686-692, Feb. 2003.

Flores et al., Paclitaxel sensitivity of breast cancer cells requires efficient mitotic arrest and disruption of Bcl-xL/Bak interaction, Breast Cancer Res Treat (2012) 133:917-928.

Jacquemier et al., Protein expression, survival and docetaxel benefit in node-positive breast cancer treated with adjuvant chemotherapy in the FNCLCC-PACS 01 randomized trial, Breast Cancer Research 2011, 13:R109.

Li et al., Systematic expression analysis of genes related to multidrug-resistance in isogenic docetaxel- and adriamycin-resistant breast cancer cell lines, Mol Biol Rep (2013) 40:6143-6150.

Longley et al., Molecular mechanisms of drug resistance, Journal of Pathology 2005; 205: 275-292.

Pascal et al., Correlation of mRNA and protein levels: Cell type-specific gene expression of cluster designation antigens in the prostate, BMC Genomics 2008, 9:246.

Poelman et al., Human breast cancer susceptibility to paclitaxel therapy is independent of Bcl-2 expression, Clinical Cancer Research 2000; 6:4043-4048.

Rice et al., Methods for handling multiple testing, Advances in Genetics, vol. 60, 2008,293-308.

Schmitt et al., Genetic analysis of chem oresistance in primary murine lymphomas, Nature Medecine, vol. 6, No. 8, Sep. 2000, pp. 1029-1035.

Tokuda et al., Estrogen receptor-α directly regulates sensitivity of paclitaxel in neoadjuvant chemtotherapy for breast cancer, Breast Cancer Res Treat (2012) 133:427-436.

Tominaga et al., Clinicopathological analysis of GATA3-positive breast cancers with special reference to response to neoadjuvant chemotherapy, Annals of Oncology 00: 1-7, 2012.

Tothova et al., High expression of Bcl-2 protein in acute myeloid leukemia cells is associated with poor response to chemotherapy, Neoplasma, 49, 3, 2002, 141-144.

Van Poznak et al., Assessment of molecular markers of clinical sensitivity to single-agent taxane therapy for metastatic breast cancer, Journal of Clinical Oncology, vol. 20, No. 9, May 1, 2002, pp. 2319-2326.

Yang et al., Bcl-2 expression predicts sensitivity to chemotherapy in breast cancer: a systematic review and meta-analysis, Journal of Experimental & Clinical Cancer Research 2013, 32:105.

* cited by examiner

PREDICTIVE MARKERS FOR TAXANE RESPONSIVENESS AND METHODS OF USE THEREOF

RELATED APPLICATIONS

The present invention is filed under 35 U.S.C. §371 as the U.S. national phase of International Application No. PCT/CA2010/001830, filed Nov. 19, 2010, which designated the U.S. and claims the benefit of priority to U.S. Provisional Application No. 61/263,174 filed Nov. 20, 2009, which is hereby incorporated in its entirety including all tables, figures and claims.

FIELD OF THE INVENTION

The field of the invention generally relates to compounds, compositions, method and/or kits for determining the benefit of chemotherapy treatment of cancer in a subject.

BACKGROUND OF THE INVENTION

The taxane drugs, paclitaxel and docetaxel, are front-line chemotherapeutic agents used in the treatment of breast, ovarian and lung cancers. Despite their wide-spread use there are substantial shortcomings, and include myelosuppression, neurotoxicity and the frequent development of resistance (McGrogan et al., 2008; Perez, 1999).

Improvements to taxane-based therapies are hampered by a lack of mechanistic knowledge regarding its therapeutic activity: taxanes alter microtubule dynamics and cause arrest at the G2/M phase of cell cycle (Jordan et al., 1993; Yvon et al., 1999), but how this mitotic arrest results in cell death is not clear (Gascoigne and Taylor, 2009; Pellegrini and Budman, 2005; Weaver and Cleveland, 2005).

Mechanistic insights into taxane-induced cytotoxicity will have two major clinical benefits.

Firstly, each effector molecule has the potential to predict taxane responsiveness in breast cancer patients. Identification of predictive markers is of major importance, since currently there is no rational selection of those patients most likely to benefit from taxane therapy (Aapro, 2001; Noguchi, 2006).

Secondly, knowledge of the protein-interaction networks that modulate cellular responses to taxanes may identify targets for future drug development or combination therapy.

The literature suggests that paclitaxel-induced cell death converges on the mitochondria and is regulated by the Bcl-2 family of proteins. Paclitaxel-induced mitochondrial dysfunction is initiated by the BH3-only Bcl-2 family member Bim, as demonstrated in mouse model systems (Bouillet et al., 1999; Tan et al., 2005) and in certain human cell lines (Li et al., 2005; Sunters et al., 2003), but not breast cancer cell lines (Czernick et al., 2009). Species-specific and cell-type specific differences likely dictate which signaling molecules are activated in response to paclitaxel.

Bcl-$X_L$/Bcl-2-associated death promoter (Bad) was originally identified as a Bcl-2-interacting protein (Yang et al., 1995). Bad mediates cell death in response to survival signal down-regulation and plays a key role in the growth factor regulated apoptosis of the developing nervous and immune systems (Datta et al., 2002; Zha et al., 1996). Growth factor stimulated kinases phosphorylate Bad at serine residues 112, 136 and 155 (mouse numbering), resulting in attenuation of Bad pro-death activity through sequestration by 14-3-3 proteins (Datta et al., 2000; Lizcano et al., 2000; Virdee et al., 2000; Zha et al., 1996). Loss of survival signaling results in dephosphorylation of Bad (Chiang et al., 2003; Klumpp et al., 2003; Roy et al., 2009), release from cytosolic 14-3-3 proteins (Datta et al., 2000; Peruzzi et al., 1999; Shimamura et al., 2000; Tan et al., 2000; Zha et al., 1996; Zhou et al., 2000), and subsequent migration to the mitochondria, where Bad functions as an anti-repressor to the pro-survival proteins Bcl-2, Bcl-XL and Bcl-w (Danial et al., 2008; Letai, 2008; Youle and Strasser, 2008).

Because Bad induces cell death through inhibition of anti-apoptotic proteins, Bad is designated as an "indirect" activator of apoptosis. It is through this mechanism that Bad induces apoptosis of breast cancer cells in response to loss of survival signaling mediated by epidermal growth factor (EGF) (Gilmore et al., 2002) and estrogen (Fernando and Wimalasena, 2004).

There remains a need, therefore, to provide compounds, compositions, method and/or kits for determining the benefit of chemotherapy treatment of cancer in a subject.

This background information is provided for the purpose of making known information believed by the applicant to be of possible relevance to the present invention. No admission is necessarily intended, nor should it be construed, that any of the preceding information constitutes prior art against the present invention.

SUMMARY OF THE INVENTION

The present application relates to compounds, compositions, method and/or kits for determining the benefit of chemotherapy treatment of cancer in a subject.

In accordance with one aspect of the present invention, there is provided a method for determining the benefit of chemotherapy in a subject, said method comprising: determining an amount of Bad in a sample from said subject, wherein the determination of the benefit of chemotherapy is indicated by the level of Bad in said sample.

In accordance with another aspect of the present invention, there is provided a method for determining whether a subject will benefit from taxane treatment for breast cancer comprising: determining the amount of Bad present in a sample of the subject; wherein if the amount of Bad present in the sample of the subject is high, then the individual will benefit from the taxane treatment for breast cancer.

In accordance with another aspect of the present invention, there is provided a method for a treating a subject having breast cancer, said method comprising: obtaining a sample from said patient, determining an amount of Bad in said sample, and subsequently administering at least one chemotherapeutic agent therapeutic agent to the subject, wherein, if the level of Bad determined in the sample is high then the at least one therapeutic agent subsequently administered to the patient comprises a taxane, and if the level of Bad determined in the sample is low then the at least one chemotherapeutic agent subsequently administered to the patient does not comprise a taxane.

In accordance with another aspect of the present invention, there is provided a use of a taxane for a treating a subject having breast cancer, comprising: obtaining a sample from said patient, determining an amount of Bad in said sample, wherein if the level of Bad determined in the sample is high then the at least one chemotherapeutic agent comprising a taxane is suitable for administration to said patient, and wherein if the level of Bad determined in the sample is low then the at least one chemotherapeutic agent not comprising a taxane is suitable for administration to said subject.

In accordance with another aspect of the present invention, there is provided a method comprising: obtaining a sample from a subject; contacting the sample with an antibody to Bad to form a complex between the antibody and Bad present in the sample; measuring the complexes formed to determine an amount of Bad in the sample; and determining the benefit of chemotherapy in the subject, wherein the determination of the benefit of chemotherapy is indicated by the level of Bad in said sample.

In accordance with another aspect of the present invention, there is provided a kit, comprising: instructions for determining the amount of Bad in a sample from a subject; and a reagent for measuring the amount of Bad in said sample, wherein the determination of the benefit of taxane treatment is indicated by the level of Bad in the sample wherein a determination of the benefit of chemotherapy is indicated by the level of Bad in said sample.

In accordance with another aspect of the present invention, there is provided a method for determining the benefit of chemotherapy in a subject, said method comprising: determining an amount of Bik in a sample from said subject, wherein the determination of the benefit of chemotherapy is indicated by the level of Bik in said sample.

In accordance with another aspect of the present invention, there is provided a method for determining whether a subject will benefit from taxane treatment for breast cancer comprising: determining the amount of Bik present in a sample of the subject; wherein if the amount of Bik present in the sample of the subject is high, then the individual will benefit from the taxane treatment for breast cancer.

In accordance with another aspect of the present invention, there is provided a method for a treating a subject having breast cancer, said method comprising: obtaining a sample from said patient, determining an amount of Bik in said sample, and subsequently administering at least one chemotherapeutic agent therapeutic agent to the subject, wherein, if the level of Bik determined in the sample is high then the at least one therapeutic agent subsequently administered to the patient comprises a taxane, and if the level of Bik determined in the sample is low then the at least one chemotherapeutic agent subsequently administered to the patient does not comprise a taxane.

In accordance with another aspect of the present invention, there is provided a use of a taxane for a treating a subject having breast cancer, comprising: obtaining a sample from said patient, determining an amount of Bik in said sample, wherein if the level of Bik determined in the sample is high then the at least one chemotherapeutic agent comprising a taxane is suitable for administration to said patient, and wherein if the level of Bik determined in the sample is low then the at least one chemotherapeutic agent not comprising a taxane is suitable for administration to said subject.

In accordance with another aspect of the present invention, there is provided a method comprising: obtaining a sample from a subject; contacting the sample with an antibody to Bik to form a complex between the antibody and Bik present in the sample; measuring the complexes formed to determine an amount of Bik in the sample; and determining the benefit of chemotherapy in the subject, wherein the determination of the benefit of chemotherapy is indicated by the level of Bik in said sample In accordance with another aspect of the present invention, there is provided a kit, comprising: instructions for determining the amount of Bik in a sample from a subject; and a reagent for measuring the amount of Bik in said sample, wherein the determination of the benefit of taxane treatment is indicated by the level of Bik in the sample wherein a determination of the benefit of chemotherapy is indicated by the level of Bik in said sample.

BRIEF DESCRIPTION OF THE DRAWINGS

Embodiments of the present invention will now be described, by way of example only, with reference to the attached Figures, wherein.

Figure 1:
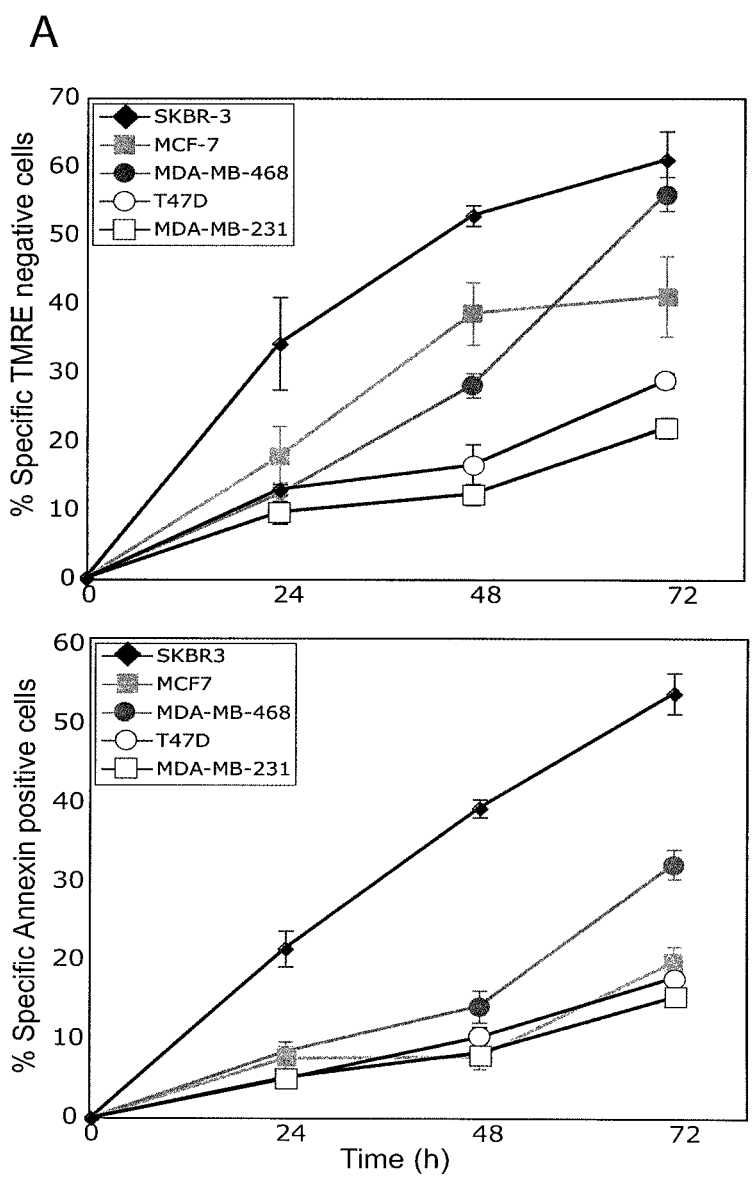
FIG. 1—Expression of pro-apoptotic Bim and Bad correlate with paclitaxel sensitivity. (A) Indicated breast carcinoma cell lines were treated with 25 nM paclitaxel for the indicated amount of time and assessed for mitochondrial depolarization (upper—TMRE negative) or phosphatidyl serine externalization (lower—annexin V positive) and graphed relative to control untreated cells. The data are represented as mean+/−standard deviation (SD). Shown is an average of 3 independent experiments. (B) Untreated whole cell lysates were subjected to SDS-PAGE western blot and analyzed with the indicated antibodies FIG. 2—Bad plays a significant role in paclitaxel-induced cell death. (A) Knock-down efficiencies in MCF-7 breast carcinoma cell lines transfected with non-specific (N.S.) or specific indicated targets were assessed by western blot analyses (upper). Apoptotic mitochondrial depolarization in the absence or presence of 25 nM paclitaxel was determined by measurement of TMRE fluorescent FACS analysis (lower). (B) MCF-7 cells were transfected with siRNAs corresponding to non-specific sequence (N.S.) or the indicated BH3-only target sequences and apoptosis was assessed after 48 hour treatment with paclitaxel. Shown is an average of 3 independent experiments. # represents P=0.1 compared to non-specific siRNA control. * represents P=0.0005 compared to non-specific siRNA control (C) Similar to B, using 2 independent siRNA target sequences to Bad. Shown is an average of 3 independent experiments. * represents P=0.0005 compared to non-specific siRNA control. + represents P=0.0025 compared to non-specific siRNA control (D) Similar to B assessing effect of Bad depletion on paclitaxel responsiveness in indicated cell lines. Shown is a representative of 2 independent experiments done in triplicate. All data are represented as mean+/−SD.
Figure 1:
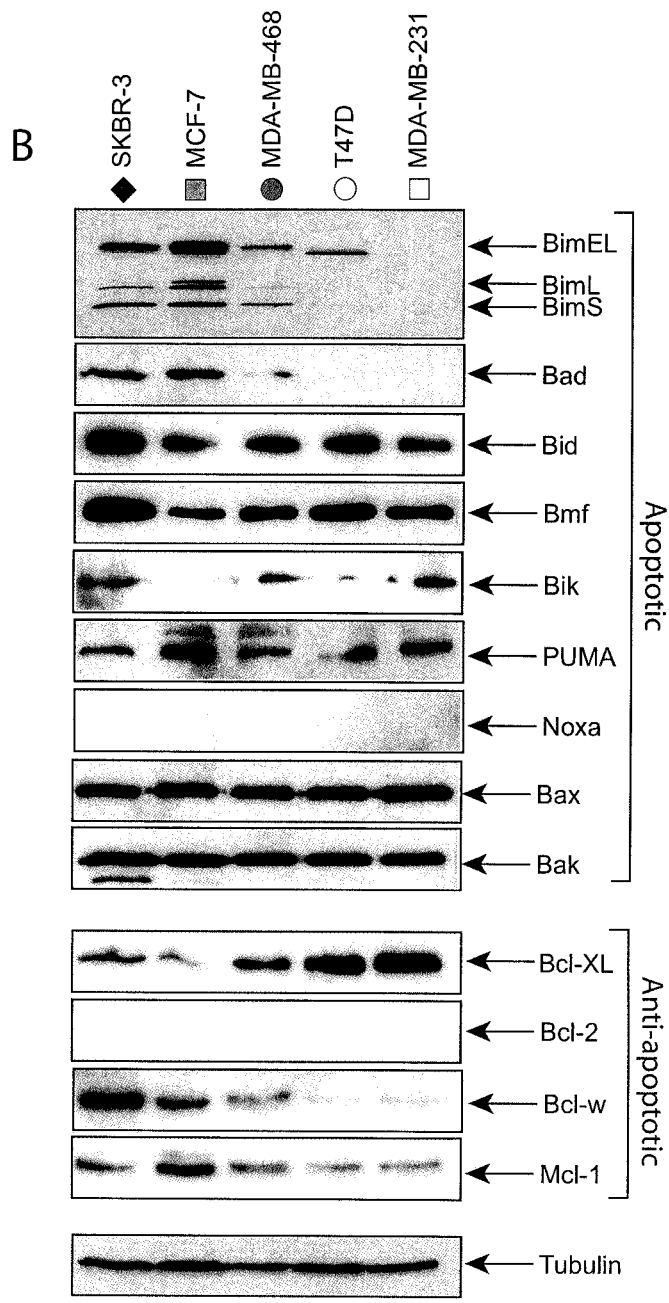

In the Detailed Description that follows, the numbers in bold face type serve to identify the component parts that are described and referred to in relation to the drawings depicting various embodiments of the invention. It should be noted that in describing various embodiments of the present invention, the same reference numerals have been used to identify the same of similar elements. Moreover, for the sake of simplicity, parts have been omitted from some figures of the drawings.

DETAILED DESCRIPTION

As will be described in more detail below, the present invention relates to determining the benefit of chemotherapy treatment in a subject.

In one aspect, the present invention relates to determining the benefit of taxane treatment to a subject with breast cancer.

The term "determining the benefit of chemotherapy treatment" as used herein, generally refers to assessing how a patient will respond to chemotherapy treatment of cancer. The term "determining the benefit of taxane treatment" as used herein, generally refers to assessing how a patient will respond to taxane treatment of cancer. In a specific example, the chemotherapy treatment is taxane treatment to a patient with breast cancer.

The term "cancer" as used herein, refers to or describes the physiological condition in a mammal that is typically characterized by unregulated cell growth. Examples of cancer include but are not limited to, breast cancer. Additional examples include, but are not limited to ovarian cancer, lung cancer, lymphoma, leukemia, germ cell cancer and primary of unknown origin (PRUNK).

The term "subject" or "patient" as used herein, refers to any mammal or non-mammal that would benefit from determining the benefit from treatment, treatment, diagnosis, therapeutic monitoring and/or prognosis. In certain examples a subject or patient includes, but is not limited to, humans, farm animals, companion animals (such as cars, dogs and horses), primates and rodent (such as mice and rats). In a specific embodiment, the subject is a human. In an additional specific embodiment, the subject is female. In another example the subject is male.

The term "treatment" as used herein, refers to clinical intervention in an attempt to alter the course of the subject or cell being treated. In non-limiting examples, treatment includes preventing or delaying recurrence of disease, alleviation of symptoms, diminishment of any direct or indirect pathological consequences of the disease, preventing metastasis, decreasing the rate of disease progression, amelioration or palliation of the disease state, and remission or improved prognosis.

The term "prognosis" as used herein refers to the prediction of the likelihood of cancer-attributable death or progression, including recurrence, metastatic spread, and drug resistance, of a neoplastic disease, such as breast cancer.

The term "prognostic marker" as used herein refers to a marker that informs about the outcome of a patient in the absence of systemic therapy or portends an outcome different from that of the patients without the marker, despite empiric (not targeted to the marker) systemic therapy.

The term "predictive marker" as used herein refers to a marker that predicts that differential efficacy (benefit) of a particular therapy based on marker status.

The term "diagnosis" as used herein, refers to the identification of a molecular and/or pathological state, disease or condition, such as the identification of breast cancer, or other type of cancer.

The term "therapeutic monitoring" as used herein refers to the observation of the response of the subject to the treatment administered to it.

In one embodiment of the present application there is provided a method for determining the benefit of taxane treatment for a female breast cancer patient.

In one example, a method of the present application comprises qualitatively or quantitatively determining, analyzing or measuring a biological sample from a female breast cancer patient for the presence or absence, or amount or concentration, of one or more proteins associated with the responsiveness of the patient to taxane treatment. In one example the protein is Bad. In another example, the protein is Bik.

The determination, analysis or measurement of the protein(s) can be correlated with the benefit of taxane treatment of breast cancer in the patient.

In some examples, a patient sample is compared to a control sample.

A suitable control can be used wherein the amount of predictive marker in the control sample is indicative of the amount of predictive marker in a subject that does not have cancer.

In one example, in determining whether there is high (e.g., strong) or low (e.g., weak or absent) amount of the predictive marker, the patient sample may be compared to one or more control samples. In one example, a control sample has had know and/or established level of the predictive maker tumour staining. In one example, a control sample is a patient sample that has known and/or established levels of predictive marker tumour staining and/or known clinical outcome. In one example, a control is a cell line that has a known amount of predictive maker staining.

In some example, a control is not used and qualitative or quantitative methods are used to determine the presence or absence, or amount or concentration of the protein of interest.

In a specific example, antibodies of the present invention are immunoreactive or immunospecific for, and therefore specifically and selectively bind to a protein of interest, for example the protein Bad or the protein Bik. In one example, antibodies which are immunoreactive and immunospecific for human Bad or Bik can be used. In one example, antibodies which are immunoreactive and immunospecific for human Bik can be used. Antibodies for human Bad or Bik are preferably immunospecific. The term "antibody" and "antibodies" includes, but is not limited to, monoclonal and polyclonal antibodies. Antibodies may be derive from multiple species. For example, antibodies include rodent (such as mouse and rat), rabbit, sheep, camel, and human antibodies. In another example, antigen binding fragments which specifically bind to Bad or Bik are used. In some example, the antibodies also comprise a label. The term "label" as used herein is an identifiable substance that is detectable in an assay and that can be attached to a molecule creating a labeled molecule. The behavior of the labeled molecule can then be monitored and/or studied and/or detected.

Examples of labels include, but are not limited to, various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate. The particular label used will depend upon the type of immunoassay. Antibodies can be tagged with such labels by known methods.

The term "binds specifically" refers to high avidity and/or high affinity binding of an antibody to a specific polypeptide e.g., an epitope of Bad or an epitope of Bik. Antibody binding to its epitope on this specific polypeptide is stronger than binding of the same antibody to any other epitope, particularly those which may be present in molecules in association with, or in the same sample, as the specific polypeptide of interest. Antibodies which bind specifically to a polypeptide of interest may be capable of binding other polypeptides at weak, yet detectable, level. Such weak binding, or background binding, is readily discernable from the specific antibody binding to the compound or polypeptide of interest, e.g., by use of appropriate controls, as would be known to the worker skilled in the art.

In one example, a sample containing cancerous cells or suspected as containing cancerous cells is obtained from the breast cancer patient. Collection of such a sample is well known to the skilled worker. In a specific example, the sample is a breast tissue sample. Methods of obtaining a breast tissue sample, processing and/or storage of such a sample are also well known to the skilled worker.

Breast tissues sample may be fresh-frozen and/or formalin-fixed, paraffin-embedded tissue blocks prepared for study by immunohistochemistry (IHC). In one example, the sample is a formalin fixed and/or paraffin-embedded tumor tissue from a biopsy or surgical resection of a cancer (e.g., tumor).

The methods of the present invention may be accomplished using any suitable method or system of immunohistochemistry. Non limiting examples include automated systems, quantitative IHC, semi-quantitative IHC, and manual methods.

The term "quantitative" immunohistochemistry refers to an automated method of scanning and scoring samples that have undergone immunohistochemistry, to identify and quantitate the presence of a specified biomarker, such as an antigen or other protein. For example, to quantitate Bad and/or Bik. The score given to the sample is a numerical representation of the intensity of the immunohistochemical staining of the sample, and represents the amount of target biomarker present in the sample. As used herein, Optical Density (OD) is a numerical score that represents intensity of staining as well as the percentage of cells that are stained. As used herein, semi-quantitative immunohistochemistry refers to scoring of immunohistochemical results by human eye, where a trained operator ranks results numerically (e.g., as 0, 1 or 2).

Automated sample processing, scanning and analysis systems suitable for use with immunohistochemistry are known in the art, and may be used with the present invention. Such systems may include automated staining and microscopic scanning, computerized image analysis, serial section comparison (to control for variation in the orientation and size of a sample), digital report generation, and archiving and tracking of samples (such as slides on which tissue sections are placed). Cellular imaging systems are commercially available that combine conventional light microscopes with digital image processing systems to perform quantitative analysis on cells and tissues, including immunostained samples.

In a specific example, the detection, analysis or measurement of Bad protein within a breast tissue sample is carried out using immunohistochemistry (IHC). It will be clear to the skilled worker that other immuno assays, both qualitative or quantitative, may be used in the present invention.

In a specific example, the detection, analysis or measurement of Bik protein within a breast tissue sample is carried out using immunohistochemistry (IHC). It will be clear to the skilled worker that other immuno assays, both qualitative or quantitative, may be used in the present invention.

In one example, immunohistochemistry is carried out using tissue microarrays from formalin fixed breast tissues using a TMArrayer™.

Other examples that may be used in the detection, analysis or measurement of Bad include, but are not limited to, immunoprecipitation and mass spectrometry.

Additional examples that may be used in the detection of Bad and/or Bik include, but are not limited to, quantitative fluorescence activated cell sorting, enzyme linked immunosorbent assay, immunohistochemistry, quantitative immunohistochemistry, fluorescence resonance energy transfer, Forster resonance energy transfer, biomolecular fluorescence complementation, mass spectrometry, immunoblot assay and coimmunoprecipitation assay.

In practice, in the example in which a patient sample is determined to have high (e.g., strong) Bad tumour staining, the patient is considered a good candidate for taxane chemotherapy. In another specific example, a patient determined to have high (e.g., strong) Bad tumour staining is considered a good candidate for adjuvant-based taxane chemotherapy.

In one example, in determining whether there is high (e.g., strong) or low (e.g., weak or absent) Bad tumour staining, the patient sample may be compared to one or more control samples. In one example, a control sample has had know and/or established level of Bad tumour staining. In one example, a control sample is a patient sample that has known and/or established levels of Bad tumour staining and/or known clinical outcome. In one example, a control is a cell line that has a known amount of Bad staining.

In some example, a control is not used and qualitative or quantitative methods are used to determine the level of staining.

In another example, in practice, in the example in which a patient sample is determined to have high (e.g., strong) Bik tumour staining, the patient is considered a good candidate for taxane chemotherapy. In another specific example, a patient determined to have high (e.g., strong) Bad tumour staining is considered a good candidate for adjuvant-based taxane chemotherapy.

In one example, in determining whether there is high (e.g., strong) or low (e.g., weak or absent) Bik tumour staining, the patient sample may be compared to one or more control samples. In one example, a control sample has had know and/or established level of Bik tumour staining. In one example, a control sample is a patient sample that has known and/or established levels of Bik tumour staining and/or known clinical outcome. In one example, a control is a cell line that has a known amount of Bad staining.

In some example, a control is not used and qualitative or quantitative methods are used to determine the level of staining.

In a specific example, the taxane is paclitaxel. In another example, the taxane is docetaxel. In another example the taxane is NAB-paclitaxel (Abraxane®)

In one example of the present invention, there was significantly increased disease-free survival and overall survival of individuals, with elevated levels of Bad protein (P=0.03 and P=0.001, respectively), who had received adjuvant docetaxel-based chemotherapy. In multivariate modeling, only ER and Bad score were independent prognostic factors for disease free survival as well as overall survival. Women with low Bad tumour staining intensity had a higher rate of relapse (hazard ratio 1.96; 95% CI 1.05-3.66) and death hazard ratio (3.65; 95% CI 1.05-3.66). In one example of the present invention, there was significantly increased overall survival of individuals, with elevated levels of Bik protein (P=0.0243), who had received adjuvant docetaxel-based chemotherapy.

Continued treatment options for patients who have received taxane adjuvant therapy are well known to the skilled worker.

It will be appreciated that in some circumstances, a patient which initially responds to taxane treatment may relapse. Such a relapse can manifest is several ways, including but not limited to, reoccurrence of the primary tumour and development of metastasis. In addition to, or alternatively, an additional distinct tumour can arise.

In another specific example, in which a patient sample is determined to have low Bad tumour staining, the patient is considered to be a poor candidate for taxane chemotherapy. In this example, alternate treatment options are well known to the skilled worker. Such alternative treatments could include non-taxane cytotoxic drugs including alkylating agents, anti-metabolites, and anthracyclines.

In accordance with one aspect of the present invention, there is provided a method for determining the benefit of taxane treatment of breast cancer in a subject, said method comprising: analyzing a sample from said subject for the amount of Bad or Bik, wherein the determination of benefit of taxane treatment is determined by the level of Bad or Bik in said sample.

In accordance with one aspect of the present invention, there is provided a method comprising: a) obtaining a breast tissue sample from a subject with, or suspected as having, breast cancer; b) contacting the sample with an antibody to Bad or Bik to form a complex between the antibody and Bad or Bik present in the sample; c) measuring the complex formed to determine an amount of Bad or Bik in the sample; and d) determining the benefit of taxane treatment of breast cancer in said subject, wherein the determination of benefit of taxane treatment is determined by the level of Bad or Bik in said sample.

In accordance with another aspect of the present invention, there is provided a method comprising: a) obtaining a breast tissue sample from a subject with, or suspected as having, breast cancer; b) analyzing the sample using a machine wherein said machine having a detector set to detect a complex formed between an antibody to Bad or Bik and the sample to obtain an amount of Bad or Bik in the sample; c) determining the benefit of taxane treatment of breast cancer in a subject, wherein the determination of the benefit of taxane treatment is determined by the level of Bad in said sample.

In one example the sample is analyzed by light microscopy by direct examination or by image capture and analysis, or by fluorescent microscopy using direct examination of by image capture and analysis.

In another embodiment, Bad contributes to paclitaxel-induced cytotoxicity of breast cancer cell lines. Specific examples of cell lines include MCF-7, MDA-MB-468 and SKBR-3.

In one example, siRNA duplexes targeted against Bad significantly reduced loss of mitochondrial electrochemical potential in response to paclitaxel.

The term siRNA (short interfering RNA) or siRNA duplexes, as used herein has the same meaning as typically in the art. i.e. the term siRNA refers to double stranded RNA complex. Often, the complex has 3'-overhangs. In one example, siRNA are commercially available.

In one embodiment, Bad contributed to paclitaxel-induced apoptosis via a mechanism that was independent of interactions with mitochondria or Bcl-XL. It was observed that Bad stimulated G1 exit with subsequent progression into G2/M. While not wishing to be bound by theory, this pro-proliferative signal ensured that cells underwent mitotic arrest, which is a requirement for paclitaxel to trigger a cell death signal.

Methods of the present invention are conveniently practiced in the form of a kit. Such a kit preferably contains antibodies for Bad and instructions for the use thereof. In a specific example, the kit further comprises at least one control sample for Bad.

In another example, a kit contains antibodies for Bik and instructions for the use thereof. In a specific example, the kit further comprises at least one control sample for Bik.

In accordance with one aspect of the present invention there is provided a kit for determining the benefit of taxane treatment in a patient with breast cancer, comprising: a) instructions for determining the amount of Bad or Bik in a breast tissue sample from said patient; b) a reagent for measuring the amount of Bad or Bik in said breast tissue sample, wherein the determination of the benefit of taxane treatment is indicated by the level of Bad in the sample. In one example, said reagent is an antibody to Bad. In one example, said reagent is an antibody to Bik. In one example positive and/or negative control samples are also included in the kit.

To gain a better understanding of the invention described herein, the following examples are set forth. It should be understood that these examples are for illustrative purposes only. Therefore, they should not limit the scope of this invention in anyway.

EXAMPLES

Experimental Procedure

Reagents.

Antibodies to Bim, Bid, Bmf, Bik, PUMA, Noxa, Bcl-XL, Bcl-2 and Bcl-w were from Cell Signaling Technologies. Antibodies to Bad were from Sigma and Cell Signaling Technologies. Antibodies to Bax and Bak were from Santa Cruz.

Antibodies to Mcl-1 and tubulin were from Sigma. siRNA duplexes were purchased from Qiagen. TMRE, annexin V, DAPI and propidium iodide were purchased from Invitrogen.

Apoptosis Assays.

Apoptosis assays were performed as described previously (Czernick et al., 2009). Briefly, breast cancer cell lines were treated with dimethyl sulfoxide (DMSO) vehicle control or 25 nM paclitaxel, which corresponds to a clinically relevant dose (Blagosklonny and Fojo, 1999; Jordan et al., 1996). After treatment, samples were divided and analyzed for apoptosis. Apoptosis was evaluated by fluorescence-activated cell sorting (FACS) analysis using the following apoptotic markers: (i) mitochondrial dysfunction [loss of mitochondrial electrochemical potential and decreases in tetramethyl rhodamine ethyl ester (TMRE)]. Percent specific TMRE loss was determined as (% TMRE negative cells of treated sample-% TMRE negative cells of untreated control sample); (ii) increases in phosphatidylserine externalization (Annexin V). Percent specific annexin V positivity was determined as (% annexin V positive cells of treated sample-% annexin V positive cells of untreated control sample).

siRNA Mediated Knock-Down Assays.

Cells were plated in a 24 well dish the day before transfection. Validated siRNAs were purchased from Qiagen and transient transfections were done according to the manufacturers protocol using 5 nM siRNA complexed with HiPerFect (Qiagen). The day after transfection, cells were treated with or without 25 nM paclitaxel for the indicated time points.

Co-Immunoprecipitation.

Cells were treated as indicated and lysed in 2% CHAPS Lysis Buffer (10% glycerol, 20 mM Tris pH 7.4, 137 mM NaCl, 2 mM EDTA, 2% CHAPS [3-[(3-Cholamidopropyl)dimethylammonio]-1-propanesulfonate] and protease inhibitor. Cell lysate was centrifuged in a benchtop microfuge at 1200 rpm for 5 minutes and supernatant was incubated with indicated antibodies. Immune complexes were recovered by incubation to protein A-sepharose, denatured and analyzed on western blots as described previously (Czernick et al., 2009).

Subcellular Fractionation.

Cells were treated as indicated and then subcellular fractionation was performed as previously described (Goping et al., 1998). Briefly, cells were homogenized in HIM buffer (200 mM mannitol, 70 mM sucrose, 1 mM EGTA, 10 mM Hepes pH 7.4). Nuclei and unbroken cells were removed by centrifugation at 700×g for 10 minutes. The cleared lysate was then fractionated into supernatant (cytosol/light membranes) and pellet (heavy membranes).

Microarray Analysis.

The DataSet SOFT file corresponding to docetaxel sensitive and resistant breast cancers (Chang et al, 2003) was downloaded from Gene Expression Omnibus at the National Center for Biotechnology information (www.ncbi.nlm.nih.gov/sites/GDSbrowser?acc=GDS360). Microarray expression data were imported into Excel (Microsoft) and individual expression values were recovered for BCL-2 family members. Cluster analysis was performed using CLUSTER 3.0 (open source software was downloaded from http://bonsai.ims.u-tokyo.ac.jp/~mdehoon/software/cluster/software.htm#ctv) (de Hoon et al., 2004; Eisen et al., 1998) and results were presented using Java Tree View (http://jtreeview.sourceforge.net/) (Saldanha, 2004).

DNA Content Analysis by Propidium Iodide Staining.

Samples were fixed at −20° C. in ice-cold 70% ethanol for a minimum of 24 hours. After fixation, the samples were stained with 20 ug/ml propidium iodide, 2 mg/ml RNase, 0.1% Triton X-100 in PBS for 30 minutes at 4° C. Samples were analyzed in the FL-2 channel on the FACScan as previously described, with the exception that doublet discrimination was achieved by gating on the smaller width G2 cells as determined by analysis of pulse width versus pulse area (Goping et al., 2008).

Immunohistochemistry and Survival Analysis.

Tissue micoarrays were made from formalin fixed breast tissues in triplicate 0.6 mm cores using the TMArrayer™. Tissues on slides were deparaffinized in xylene and rehydrated in decreasing concentrations of ethanol to water. Endogenous peroxidase was quenched in 0.3% $H_2O_2$ for 10 minutes. For antigen retrieval, slides were placed in boiling citrate buffer pH 6.0 for 10 minutes followed by rinsing in water for 10 minutes. Tissues were incubated with the BAD antibody (Cell Signaling Technology) at a dilution of 1/25 at 4° C. overnight in a humidified container or with Bik antibody (Cell signaling Technology) at a dilution of 1/50 at room temperature in a humidified container. Slides were washed 2 times in PBS for 5 minutes. For the secondary antibody, Anti-Rabbit EnVision+System-HRP (Dako) was incubated on the tissues at room temperature for 30 minutes. Slides were washed 2 times in PBS and then tissues were incubated with DAB (Dako) for 10 minutes. Slides were rinsed in water for 10 minutes followed by a soak in 1% Copper Sulfate for 5 minutes. Haematoxylin was used to counterstain the tissues. Slides were dipped 3 times in saturated Lithium Carbonate, rinsed in water, dehydrated in increasing concentrations of ethanol and xylene and coverslipped. Staining intensity was scored as 0 (absent), 1 (weak), or 2 (strong). The average of the three samples was used to define the staining for each patient. Receiver operator curve analysis was used to select the optimal cut point to dichotomize a continuous variable. Using ROC, an optimized cutpoint of 0.57 was chosen for Bad expression and an optimized cutpoint of 0.1 was chosen for Bik expression, and patients were analyzed based on this cutpoint. Multivariate analysis including age, stage, grade, and ER status was conducted using SAS v 9.1.3 (SAS Institute Inc. Cary, N.C.).

Results and Discussion

To investigate which BH3-only proteins are involved in paclitaxel-induced apoptosis, a panel of five validated breast cancer cell lines acquired from Dr. Gordon Mills (M.D. Anderson Cancer Center, U. of Texas) was analyzed; validated cells were used to avoid any controversy with respect to lineage authenticity (Graham et al., 1986; Osborne et al., 1987).

Each cell line was treated with 25 nM of paclitaxel, which induces a clinically relevant intracellular accumulation of the drug in tissue culture conditions (Derry et al., 1998; Jordan et al., 1996). After the indicated amount of time, apoptosis was assessed by measuring mitochondrial electrochemical potential loss (TMRE loss) and phosphatidyl serine externalization (annexin V positivity) (FIG. 1A). The relative paclitaxel sensitivities of the various breast cancer cell lines, in rank order of increasing sensitivity were MDA-MB-231, T47-D, MDA-MB-468, MCF-7 and SKBR-3. Of note, while the MCF-7 cell line displayed a robust loss of mitochondrial potential in response to paclitaxel, phosphatidyl serine externalization was blunted because these cells do not express caspase 3 (Janicke et al., 1998); however, based on mitochondrial dysfunction and cellular morphology, it was clear that paclitaxel induced significant death of these cells.

Figure 2:
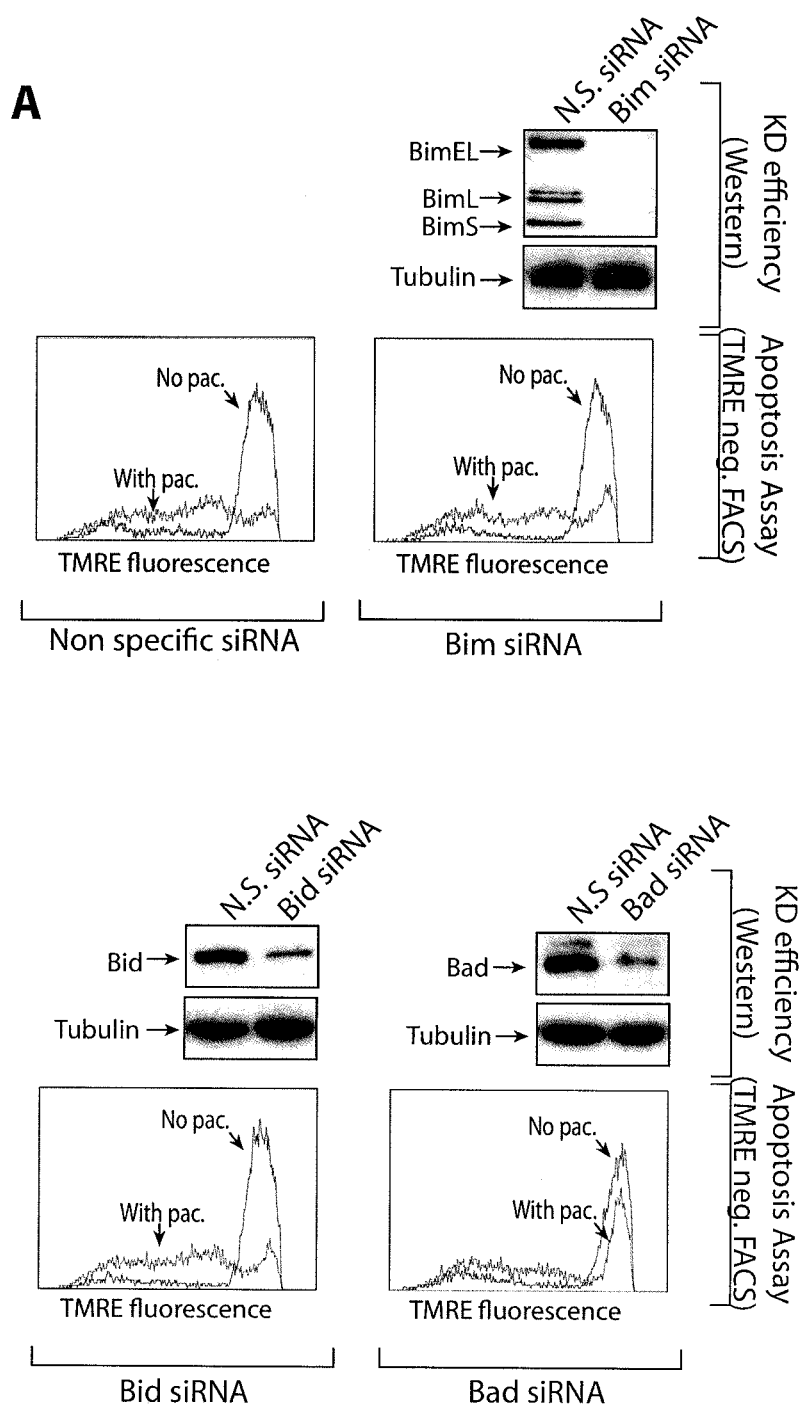
Figure 2:
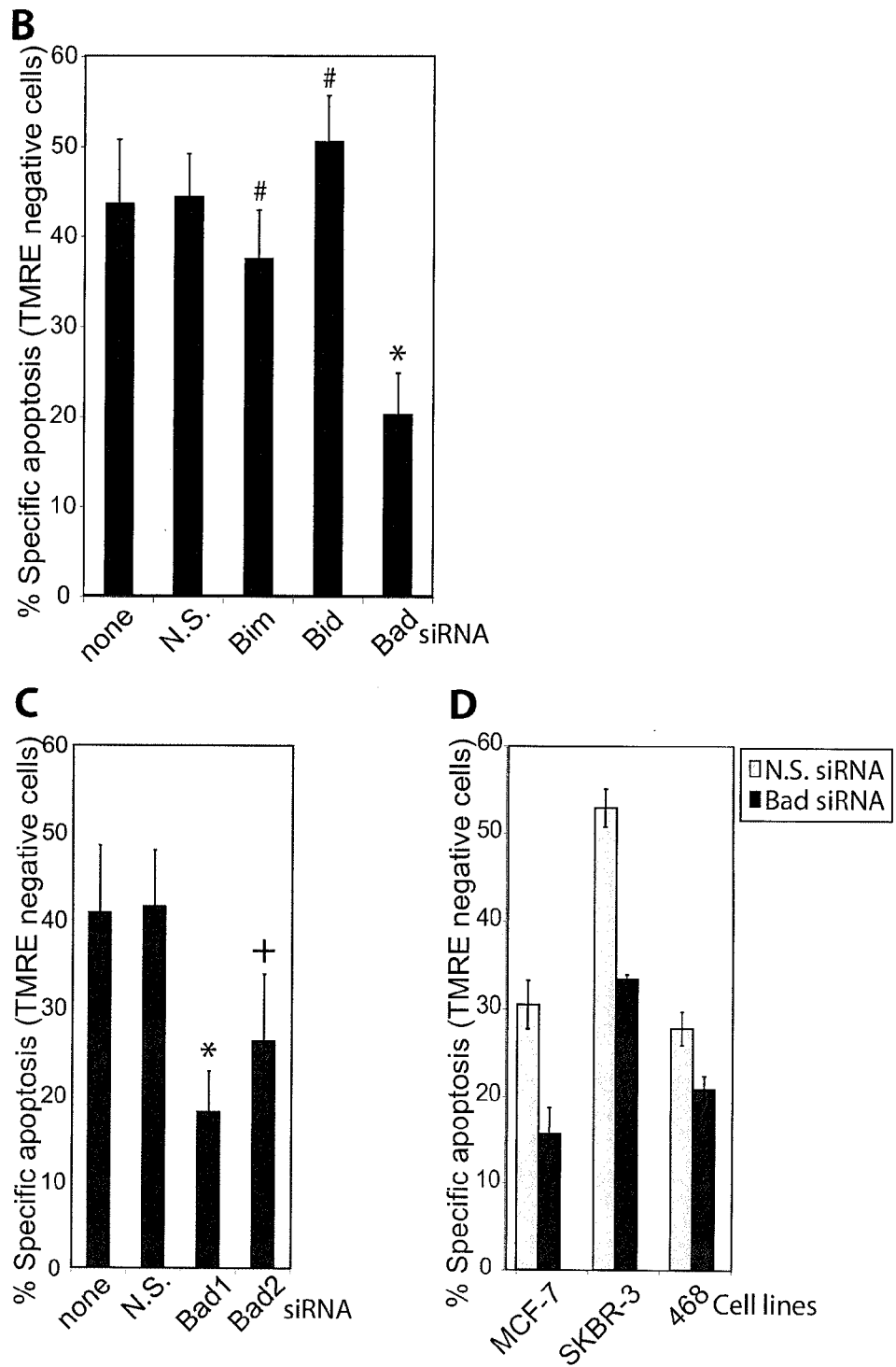

Correlations between the expression levels of Bcl-2 family proteins in these cell lines with drug sensitivity were determined. As can be seen in FIG. 1B, protein expression levels were widely variable. Of the BH3-only proteins, only the expression of Bim and Bad correlated with sensitivity to paclitaxel. Since it has previously been reported that Bim depletion did not protect these cells from paclitaxel-induced cytotoxicity (Czernick et al., 2009), loss of function studies were pursued to assess whether Bad expression contributed to cellular sensitivity to paclitaxel.

siRNAs was used to test the contribution of Bad expression towards paclitaxel cytotoxicity. siRNA duplexes targeted against Bad, Bim and Bid were transiently transfected into the MCF-7 breast cancer cell line. Knock-down efficiency was monitored by western blotting (FIG. 2A, upper). Paclitaxel-mediated cell death as assessed by loss of mitochondrial electrochemical potential was significantly reduced only in cells transfected with Bad-targeted siRNA and not with siRNA targeted against Bim, Bid or a negative control sequence (FIG. 2A, see arrow and FIG. 2B). Significant reduction of paclitaxel-mediated apoptosis was also induced by an independent siRNA target sequence to Bad (FIG. 2C, Bad2). Finally, to determine whether multiple breast carcinoma cell lines were dependent on Bad expression for sensitivity to paclitaxel, SKBR-3 and MDA-MB-468 in addition to MCF-7 cells were tested (FIG. 2D). Depletion of Bad protected all of these cell lines from paclitaxel-induced cytotoxicity, indicating that Bad plays a significant role in paclitaxel-induced cell death in multiple breast cancer cell lines.

Given that Bad levels contributed to paclitaxel responsiveness in cell line model systems, a clinical evaluation of Bad protein levels as a prognostic marker in taxane treated breast cancer was pursued.

Figure 3:
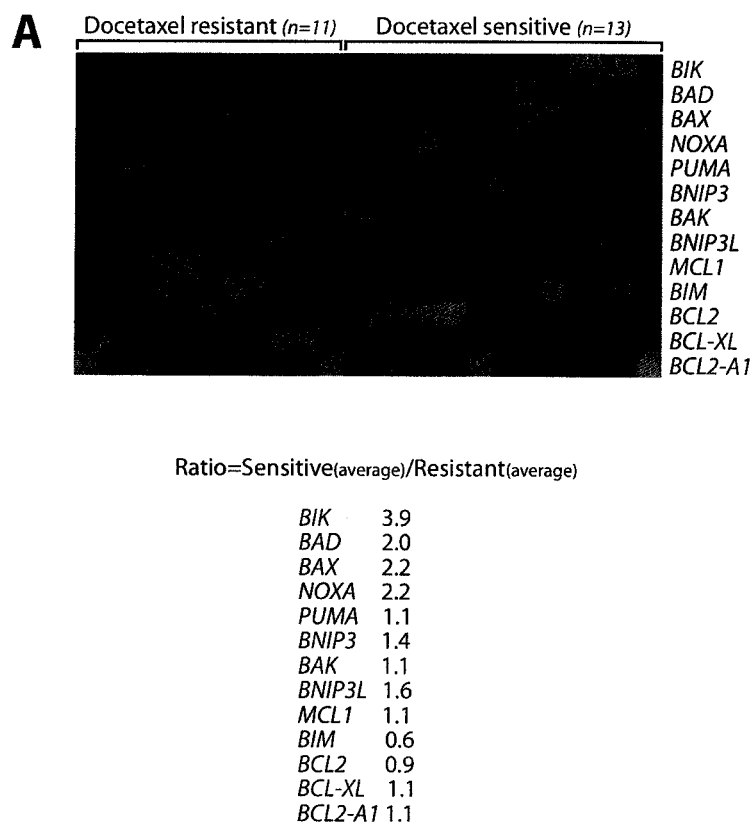
FIG. 3 Bad and Bik expression correlates with positive clinical outcomes in breast cancer patients. (A) Gene expression analysis for the indicated genes are indicated and were acquired from (Chang et al., 2003). Increased or decreased expression is indicated by intensity of red or green signal, respectively. The average gene expression values for sensitive tumor and resistant tumors are expressed as a ratio. (B) Kaplan-Meyer curves for relapse free and overall survival relative to Bad levels are shown in 180 women with early stage breast cancer receiving adjuvant docetaxel treatment.
Figure 3:
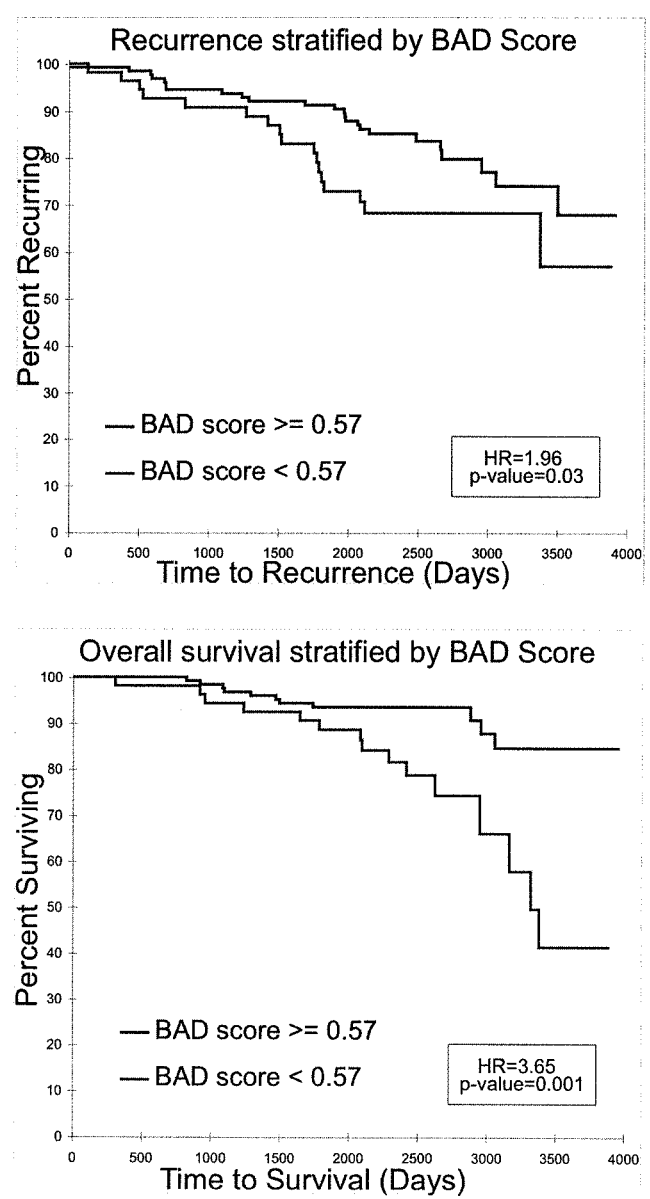

A data set compiled by Chang et al. was queried, which comprised gene expression data from 24 tumour samples from breast cancer patients prior to neoadjuvant docetaxel treatment (Chang et al., 2003). Following treatment, the samples were stratified as sensitive or resistant based on residual tumour volume of less or greater than 25%, respectively. Expression levels of Bcl-2 family members were assessed, and similar to Chang et al, observed elevated levels of Bax mRNA in association with tumour regression. Of the other family members that were tested, only Bad and Bik mRNA levels correlated with positive outcome (FIG. 3A). Bad mRNA levels on average were 2-fold higher in tumours classified as docetaxel sensitive.

To determine the prognostic value of elevated Bad protein expression, Bad protein levels were evaluated with respect to clinical response to taxane treatment from an independent study.

Figure 5:
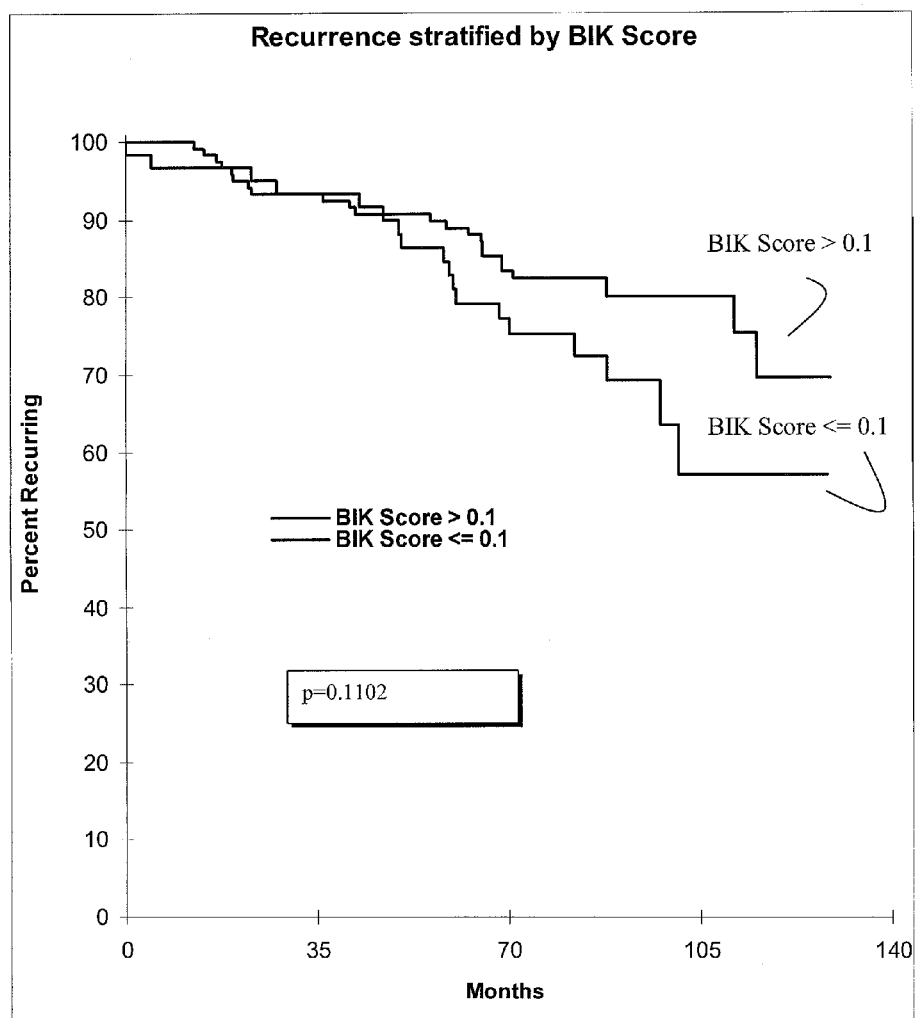
FIG. 5 is a graph depicting recurrence stratified by Bik Score. Kaplan-Meier curves for overall survival for Bik positive cases compared to Bik negative cases of 180 women with early stage breast cancer receiving adjuvant docetaxel treatment are shown. Patients were stratified by Bik immunohistochemistry reactivity. The black lines (upper lines) represent 120 patients with Bik expressing tumors. The red lines (lower lines) represent 60 patients with weak or no Bik expression.
Figure 6:
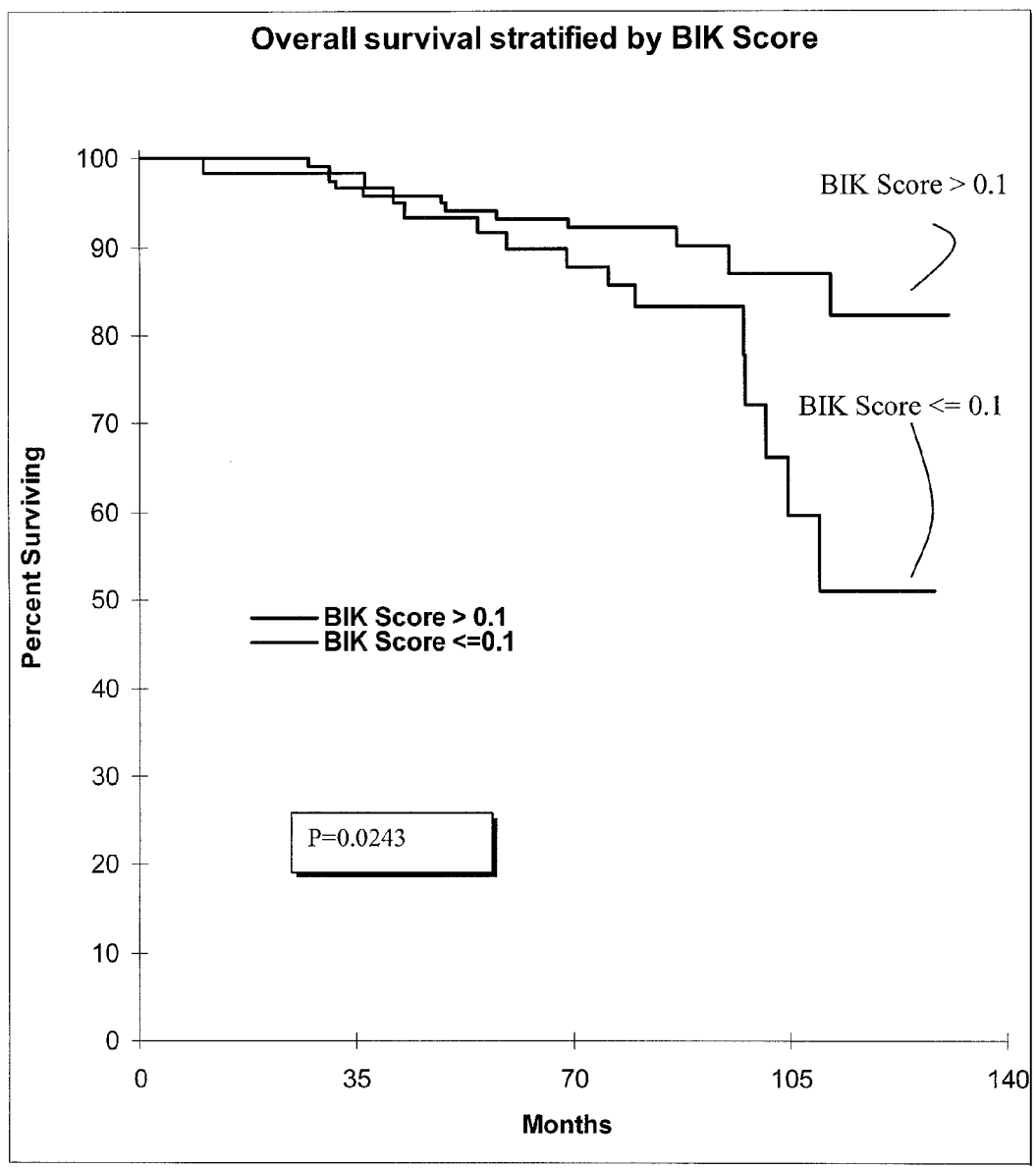
FIG. 6 is a graph depicting survival stratified by Bik Score. Kaplan-Meier curves for overall survival for Bik positive cases compared to Bik negative cases of 180 women with early stage breast cancer receiving adjuvant docetaxel treatment are shown. Patients were stratified by Bik immunohistochemistry reactivity. The black lines (upper lines) represent 120 patients with Bik expressing tumors. The red lines (lower lines) represent 60 patients with weak or no Bik expression.

After local research ethics board approval, 180 formalin fixed paraffin embedded primary tumors from patients who had received adjuvant docetaxel-based chemotherapy at a single institution (Cross Cancer Institute, Edmonton, Canada) for whom complete baseline information and long-term outcome data were available, were examined. Bad staining (FIG. 3B) and Bik staining (FIGS. 5 and 6) was scored semi-quantitatively by a breast cancer pathologist blinded to clinical outcomes.

Significantly increased disease-free survival and overall survival of individuals with elevated levels of Bad protein ($P=0.03$ and $P=0.001$, respectively) were determined. In multivariate modeling, only ER and Bad score were independent prognostic factors for disease free survival as well as overall survival. Women with low Bad tumour staining intensity had a higher rate of relapse (hazard ratio 1.96; 95% CI 1.05-3.66) and death hazard ratio (3.65; 95% CI 1.05-3.66).

Together, analyses of these 2 independent data sets demonstrated that elevated Bad levels correlate with patient responsiveness to docetaxel treatment in both the neoadjuvant and adjuvant setting.

Additionally, there was significantly increased overall survival of individuals, with elevated levels of Bik protein ($P=0.0243$), who had received adjuvant docetaxel-based chemotherapy.

Given that Bad associated with clinical outcome, the mechanism of Bad activity was examined. Based on functional in vitro assays, it was reasonable to propose that taxanes induced the elimination of breast cancer cells through stimulation of Bad pro-apoptotic activity.

Figure 4:
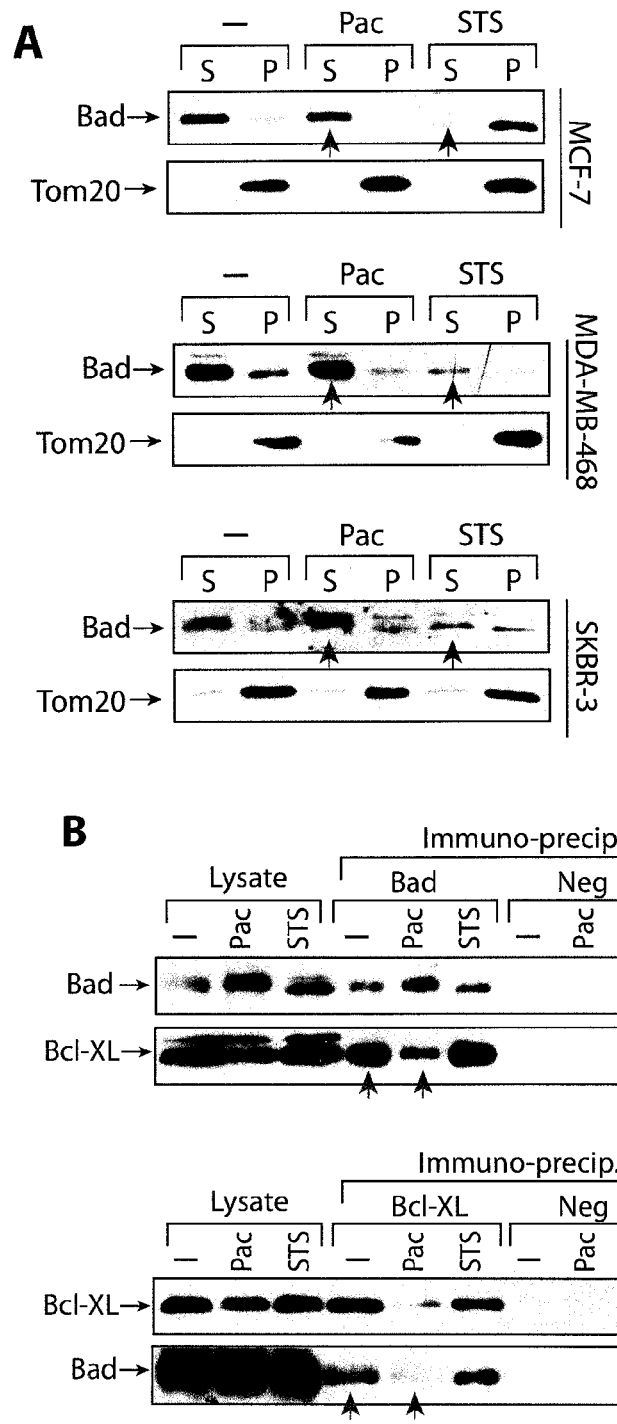
FIG. 4 Bad mediates paclitaxel cytotoxicity through a non-apoptotic pathway. (A) Paclitaxel does not induce Bad translocation to mitochondria. Indicated cells were treated with 25 nM paclitaxel (Pac) for 48 h or 2.5 uM staurosporine (STS) for 4 hours, and then lysed and fractionated into cytosolic supernatant (S) or heavy membrane pellet (P) fractions. Intracellular localizations of Bad or mitochondrial membrane control Tom20, were determined by western blot analyses. Arrows highlight different localization of Bad in paclitaxel vs. STS treated cells. (B) Paclitaxel does not induce Bad binding to Bcl-XL. Cells that were untreated or treated as above, were lysed and specific proteins were immunoprecipitated with antibodies against, Bad, Bcl-XL or a negative control non-expressing protein (Neg. granzyme A), and western blots were probed as indicated. Arrows highlight diminished Bad:Bcl-XL interactions in paclitaxel treated vs. STS treated cells. Shown are representative images of 5 independent experiments. (C) Bad stimulates cell cycle progression. MCF-7 cells were transfected with no siRNA (untreated), negative control siRNA (N.S.) or Bad-specific siRNA and then cell counts were determined over a time course of 96 h. The data are represented as mean+/−SD. Shown is an average of 3 independent experiments. (D) Bad stimulates G1 exit. MCF-7 cells were transfected with non-specific (N.S.) or Bad-specific siRNA, treated with or without paclitaxel for the time points indicated, then fixed, permeabilized and stained with propidium iodide. DNA content was determined by flow cytometry. Arrows highlight increased proportion of cells in G1 phase of the cell cycle in Bad-depleted cells vs. control cells and red arrows highlight decreased proportion of cells in G2/M phase of the cell cycle in Bad-depleted cells vs. control cells after G1 entry is blocked by paclitaxel treatment. Shown are representative images of 3 independent experiments.
Figure 4:
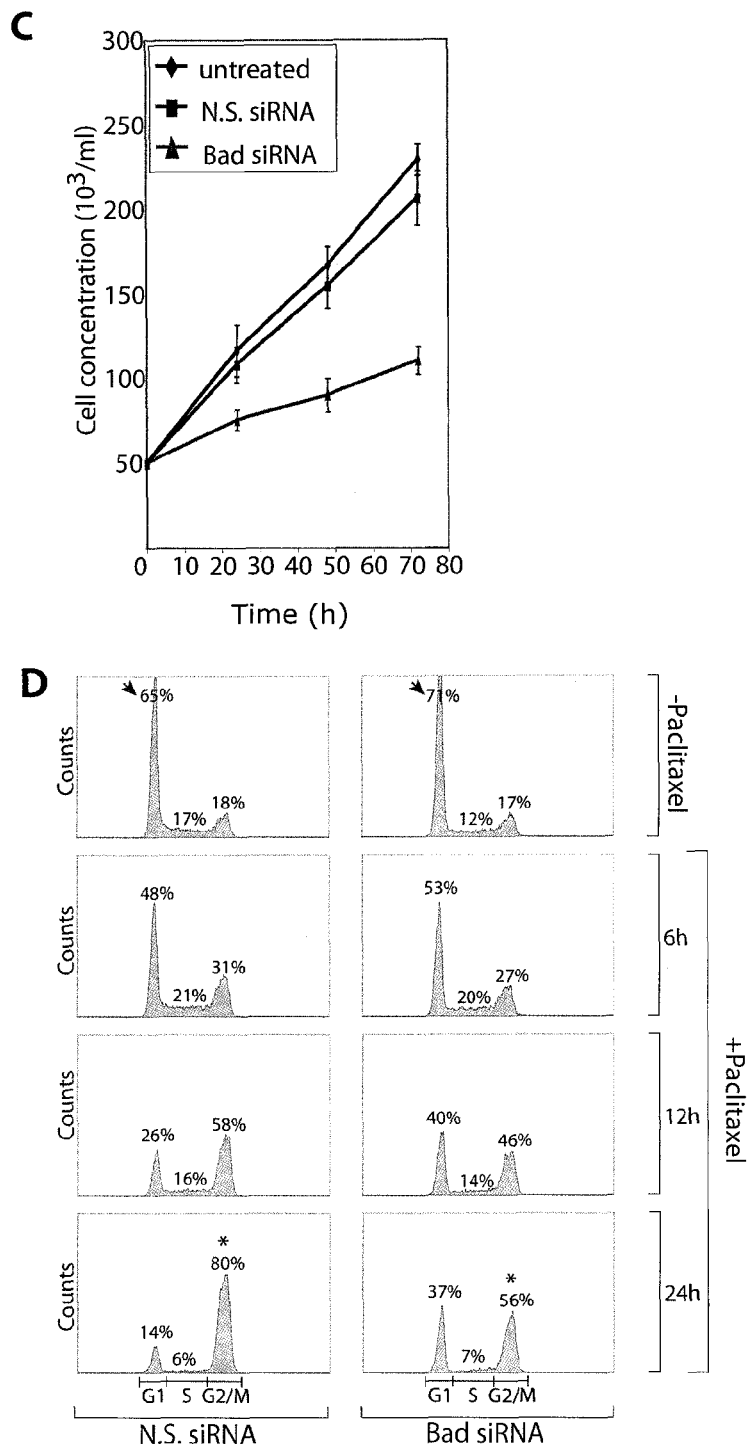

In order to characterize the mechanism of Bad pro-apoptotic activity as induced by paclitaxel, we postulated that Bad was functioning via its well-established role as an "indirect" activator of the mitochondrial apoptotic machinery. In this model, an apoptotic signal triggers translocation of Bad from the cytosol to the mitochondria, where Bad indirectly stimulates mitochondrial dysfunction by interacting with Bcl-XL, Bcl-2 and Bcl-w. As a first step, the intracellular localization of Bad in response to paclitaxel was determined. MCF-7, MDA-MB-468 and SKBR-3 cells were treated with either paclitaxel or the positive control apoptotic inducer staurosporine (STS), fractionated into cytosolic supernatant (S) and mitochondria-containing heavy membrane pellet (P) fractions, and Bad localization was determined by Western blotting (FIG. 4A). Bad was cytosolic in untreated cells and migrated to mitochondria in response to STS. Surprisingly however, unlike STS, paclitaxel treatment did not induce mitochondrial translocation of Bad (FIG. 4A, compare arrows indicating that paclitaxel cytotoxicity was not dependent on Bad interactions with components of the mitochondrial apoptotic machinery.

Next, the interaction of Bad with its most relevant downstream target, Bcl-XL (Kelekar et al., 1997; Zha et al., 1997) was investigated. Co-immunoprecipitation studies showed that Bad interacted with Bcl-XL in untreated cells, and remained as a complex in response to STS treatment. In contrast, paclitaxel treatment resulted in decreased association of Bad and Bcl-XL (FIG. 4B compare green arrows), indicating that paclitaxel-induced cell death did not require Bad-dependent inhibition of Bcl-XL.

It was found that paclitaxel-treated cells had reduced levels of Bcl-XL protein; an observation that has been previously reported by others (Liu and Stein, 1997). In fact, mitotic arrest-mediated repression of Bcl-XL contributes to cell death via liberation of Bax (Upreti et al., 2008). However, Bax activation occurs downstream of Bad signalling and paclitaxel-mediated reduction of Bcl-XL levels do not shed light on how Bad contributes to either taxane effects in vitro, or patient responsiveness in the clinical setting. Instead, while not wishing to be bound by theory, these results indicate that paclitaxel induces a Bad-dependent cell death pathway, which is distinct from its well-known role as an indirect activator of Bax and mitochondrial dysfunction.

The contribution of Bad to paclitaxel-induced cell death was examined. Depletion of Bad decreased the doubling times of cells in culture (FIG. 4C). Cell cycle DNA content analyses demonstrated that a consistently higher proportion of Bad-depleted cells were in the G1 stage of the cell cycle (FIG. 4D, compare arrows in top two plots. These results suggested that Bad may be required for G1 exit.

To verify that the increased proportion of cells in G1 was due to delayed G1 exit and not increased G1 entry, G1 entry was inhibited by arresting cells at G2/M with paclitaxel. Cells were incubated for up to 24 hours in paclitaxel, which induced mitotic arrest, but was not enough time to induce apoptosis. In time course analyses, the progression of cells from G1 through S to G2/M was delayed in Bad-depleted cells relative to control transfected cells. This delayed cell cycle progression resulted in a lower proportion of Bad-depleted cells in G2/M, relative to control cells (FIG. 4D, compare asterisks). Based on these observations, and again while not wishing to be bound by theory, it was concluded that Bad contributes to cell cycle progression by facilitating exit from the G1 phase of the cell cycle and is supported by a similar role of Bad in rat fibroblasts (Chattopadhyay et al., 2001).

The pro-proliferative function of Bad mediate paclitaxel cytotoxicity was examined.

Taxanes must induce mitotic arrest in order to trigger apoptosis (Blajeski et al., 2001; Gascoigne and Taylor, 2008; Henley et al., 2007; Jordan et al., 1996; Swanton et al., 2007). Thus, the results herein indicate that Bad stimulation of cell cycle progression facilitates paclitaxel-induced mitotic arrest and subsequent apoptosis. The determination that Bad contributes to taxane-induced death of breast cancer cells through a non-apoptotic mechanism has significant implications with respect to the development of future therapies.

In particular, and while not wishing to be bound by theory, Bad may be a specific regulator of breast cell growth. While it is shown here that Bad can stimulate proliferation, substantial evidence exists that Bad also mediates apoptosis of breast cells. For example, loss of EGFR signalling triggers a Bad stimulated cell death pathway in a mouse model system (Ranger et al., 2003), and human mammary epithelial cells (Gilmore et al., 2002). Additionally, blockade of estradiol signalling induced Bad-dependent death of MCF-7 cells (Fernando and Wimalasena, 2004), with elevated levels of Bad protein correlating with increased survival of tamoxifen-treated breast cancer patients (Cannings et al., 2007). Bad therefore stimulates an apoptotic pathway in response to EGFR and ER inhibition—two widely used breast cancer therapies. In normal breast tissue, Bad may also contribute to the development of the mammary gland. Bad is expressed at high levels in breast cells (Kitada et al., 1998), and Bad expression is elevated in apoptotic cells of the mammary gland during involution after pregnancy and weaning (Metcalfe et al., 1999; Schorr et al., 1999).

The ability of Bad to stimulate proliferation was originally reported in 2001 (Chattopadhyay et al., 2001; Maslyar et al., 2001), but was not extensively discussed until recently (see Danial, 2009). Proliferative roles for Bad were identified through ectopic expression of Bad in chicken embryo fibroblasts and prostate cancer cells (Maslyar et al., 2001; Smith et al., 2009). Bad had been shown to function as a pro-survival factor in neuronal cells (Seo et al., 2004), and stimulate metabolism of liver and pancreatic islet cells (Danial et al., 2003; Danial et al., 2008). All together, complex mechanisms must regulate Bad pro-growth and pro-apoptotic function and as yet, the mechanism of Bad-stimulated cell growth in breast cancer cells is not known.

REFERENCES

Aapro, M. S. (2001). Adjuvant therapy of primary breast cancer: a review of key findings from the 7th international conference, St. Gallen, February 2001. Oncologist 6, 376-385.

Andreeff, M., Jiang, S., Zhang, X., Konopleva, M., Estrov, Z., Snell, V. E., Xie, Z., Okcu, M. F., Sanchez-Williams, G., Dong, J., et al. (1999). Expression of Bcl-2-related genes in normal and AML progenitors: changes induced by chemotherapy and retinoic acid. Leukemia 13, 1881-1892.

Blagosklonny, M. V., and Fojo, T. (1999). Molecular effects of paclitaxel: myths and reality (a critical review). Int J Cancer 83, 151-156.

Blajeski, A. L., Kottke, T. J., and Kaufmann, S. H. (2001). A multistep model for paclitaxel-induced apoptosis in human breast cancer cell lines. Exp Cell Res 270, 277-288.

Bouillet, P., Metcalf, D., Huang, D. C., Tarlinton, D. M., Kay, T. W., Kontgen, F., Adams, J. M., and Strasser, A. (1999). Proapoptotic Bcl-2 relative Bim required for certain apoptotic responses, leukocyte homeostasis, and to preclude autoimmunity. Science 286, 1735-1738.

Cannings, E., Kirkegaard, T., Tovey, S. M., Dunne, B., Cooke, T. G., and Bartlett, J. M. (2007). Bad expression predicts outcome in patients treated with tamoxifen. Breast Cancer Res Treat 102, 173-179.

Chang, J. C., Makris, A., Gutierrez, M. C., Hilsenbeck, S. G., Hackett, J. R., Jeong, J., Liu, M. L., Baker, J., Clark-Langone, K., Baehner, F. L., et al. (2008). Gene expression patterns in formalin-fixed, paraffin-embedded core biopsies predict docetaxel chemosensitivity in breast cancer patients. Breast Cancer Res Treat 108, 233-240.

Chang, J. C., Wooten, E. C., Tsimelzon, A., Hilsenbeck, S. G., Gutierrez, M. C., Elledge, R., Mohsin, S., Osborne, C. K., Chamness, G. C., Allred, D. C., and O'Connell, P. (2003). Gene expression profiling for the prediction of therapeutic response to docetaxel in patients with breast cancer. Lancet 362, 362-369.

Chattopadhyay, A., Chiang, C. W., and Yang, E. (2001). BAD/BCL-[X(L)] heterodimerization leads to bypass of G0/G1 arrest. Oncogene 20, 4507-4518.

Chiang, C. W., Kanies, C., Kim, K. W., Fang, W. B., Parkhurst, C., Xie, M., Henry, T., and Yang, E. (2003). Protein phosphatase 2A dephosphorylation of phosphoserine 112 plays the gatekeeper role for BAD-mediated apoptosis. Mol Cell Biol 23, 6350-6362.

Czernick, M., Rieger, A., and Goping, I. S. (2009). Bim is reversibly phosphorylated but plays a limited role in paclitaxel cytotoxicity of breast cancer cell lines. Biochem Biophys Res Commun 379, 145-150.

Danial, N. N., Gramm, C. F., Scorrano, L., Zhang, C. Y., Krauss, S., Ranger, A. M., Datta, S. R., Greenberg, M. E., Licklider, L. J., Lowell, B. B., et al. (2003). BAD and glucokinase reside in a mitochondrial complex that integrates glycolysis and apoptosis. Nature 424, 952-956.

Danial, N. N., Walensky, L. D., Zhang, C. Y., Choi, C. S., Fisher, J. K., Molina, A. J., Datta, S. R., Pitter, K. L., Bird, G. H., Wikstrom, J. D., et al. (2008). Dual role of proapoptotic BAD in insulin secretion and beta cell survival. Nat Med 14, 144-153.

Datta, S. R., Katsov, A., Hu, L., Petros, A., Fesik, S. W., Yaffe, M. B., and Greenberg, M. E. (2000). 14-3-3 proteins and survival kinases cooperate to inactivate BAD by BH3 domain phosphorylation. Mol Cell 6, 41-51.

Datta, S. R., Ranger, A. M., Lin, M. Z., Sturgill, J. F., Ma, Y. C., Cowan, C. W., Dikkes, P., Korsmeyer, S. J., and Greenberg, M. E. (2002). Survival factor-mediated BAD phosphorylation raises the mitochondrial threshold for apoptosis. Dev Cell 3, 631-643.

de Hoon, M. J., Imoto, S., Nolan, J., and Miyano, S. (2004). Open source clustering software. Bioinformatics 20, 1453-1454.

Derry, W. B., Wilson, L., and Jordan, M. A. (1998). Low potency of taxol at microtubule minus ends: implications for its antimitotic and therapeutic mechanism. Cancer Res 58, 1177-1184.

Eisen, M. B., Spellman, P. T., Brown, P. O., and Botstein, D. (1998). Cluster analysis and display of genome-wide expression patterns. Proc Natl Acad Sci USA 95, 14863-14868.

Fernando, R. I., and Wimalasena, J. (2004). Estradiol abrogates apoptosis in breast cancer cells through inactivation of BAD: Ras-dependent nongenomic pathways requiring signaling through ERK and Akt. Mol Biol Cell 15, 3266-3284.

Gascoigne, K. E., and Taylor, S. S. (2008). Cancer cells display profound intra- and interline variation following prolonged exposure to antimitotic drugs. Cancer Cell 14, 111-122.

Gascoigne, K. E., and Taylor, S. S. (2009). How do antimitotic drugs kill cancer cells? J Cell Sci 122, 2579-2585.

Gilmore, A. P., Valentijn, A. J., Wang, P., Ranger, A. M., Bundred, N., O'Hare, M. J., Wakeling, A., Korsmeyer, S. J., and Streuli, C. H. (2002). Activation of BAD by therapeutic inhibition of epidermal growth factor receptor and transactivation by insulin-like growth factor receptor. J Biol Chem 277, 27643-27650.

Goping, I. S., Gross, A., Lavoie, J. N., Nguyen, M., Jemmerson, R., Roth, K., Korsmeyer, S. J., and Shore, G. C. (1998). Regulated targeting of BAX to mitochondria. J Cell Biol 143, 207-215.

Goping, I. S., Sawchuk, T., Rieger, A., Shostak, I., and Bleackley, R. C. (2008). Cytotoxic T lymphocytes overcome Bcl-2 inhibition: target cells contribute to their own demise. Blood 111, 2142-2151.

Graham, K. A., Trent, J. M., Osborne, C. K., McGrath, C. M., Minden, M. D., and Buick, R. N. (1986). The use of restriction fragment polymorphisms to identify the cell line MCF-7. Breast Cancer Res Treat 8, 29-34.

Henley, D., Isbill, M., Fernando, R., Foster, J. S., and Wimalasena, J. (2007). Paclitaxel induced apoptosis in breast cancer cells requires cell cycle transit but not Cdc2 activity. Cancer Chemother Pharmacol 59, 235-249.

Janicke, R. U., Sprengart, M. L., Wati, M. R., and Porter, A. G. (1998). Caspase-3 is required for DNA fragmentation and morphological changes associated with apoptosis. J Biol Chem 273, 9357-9360.

Jordan, M. A., Toso, R. J., Thrower, D., and Wilson, L. (1993). Mechanism of mitotic block and inhibition of cell proliferation by taxol at low concentrations. Proc Natl Acad Sci USA 90, 9552-9556.

Jordan, M. A., Wendell, K., Gardiner, S., Derry, W. B., Copp, H., and Wilson, L. (1996). Mitotic block induced in HeLa cells by low concentrations of paclitaxel (Taxol) results in abnormal mitotic exit and apoptotic cell death. Cancer Res 56, 816-825.

Kelekar, A., Chang, B. S., Harlan, J. E., Fesik, S. W., and Thompson, C. B. (1997). Bad is a BH3 domain-containing protein that forms an inactivating dimer with Bcl-XL. Mol Cell Biol 17, 7040-7046.

Kitada, S., Krajewska, M., Zhang, X., Scudiero, D., Zapata, J. M., Wang, H. G., Shabaik, A., Tudor, G., Krajewski, S., Myers, T. G., et al. (1998). Expression and location of pro-apoptotic Bcl-2 family protein BAD in normal human tissues and tumor cell lines. Am J Pathol 152, 51-61.

Klumpp, S., Selke, D., and Krieglstein, J. (2003). Protein phosphatase type 2C dephosphorylates BAD. Neurochem Int 42, 555-560.

Letai, A. G. (2008). Diagnosing and exploiting cancer's addiction to blocks in apoptosis. Nat Rev Cancer 8, 121-132.

Li, R., Moudgil, T., Ross, H. J., and Hu, H. M. (2005). Apoptosis of non-small-cell lung cancer cell lines after paclitaxel treatment involves the BH3-only proapoptotic protein Bim. Cell Death Differ 12, 292-303.

Liu, Q. Y., and Stein, C. A. (1997). Taxol and estramustine-induced modulation of human prostate cancer cell apoptosis via alteration in bcl-xL and bak expression. Clin Cancer Res 3, 2039-2046.

Lizcano, J. M., Morrice, N., and Cohen, P. (2000). Regulation of BAD by cAMP-dependent protein kinase is mediated via phosphorylation of a novel site, Ser155. Biochem J 349, 547-557.

Maslyar, D. J., Aoki, M., and Vogt, P. K. (2001). The growth-promoting activity of the Bad protein in chicken embryo fibroblasts requires binding to protein 14-3-3. Oncogene 20, 5087-5092.

McGrogan, B. T., Gilmartin, B., Carney, D. N., and McCann, A. (2008). Taxanes, microtubules and chemoresistant breast cancer. Biochim Biophys Acta 1785, 96-132.

Metcalfe, A. D., Gilmore, A., Klinowska, T., Oliver, J., Valentijn, A. J., Brown, R., Ross, A., MacGregor, G., Hickman, J. A., and Streuli, C. H. (1999). Developmental regulation of Bcl-2 family protein expression in the involuting mammary gland. J Cell Sci 112 (Pt 11), 1771-1783.

Noguchi, S. (2006). Predictive factors for response to docetaxel in human breast cancers. Cancer Sci 97, 813-820.

Osborne, C. K., Hobbs, K., and Trent, J. M. (1987). Biological differences among MCF-7 human breast cancer cell lines from different laboratories. Breast Cancer Res Treat 9, 111-121.

Pellegrini, F., and Budman, D. R. (2005). Review: tubulin function, action of antitubulin drugs, and new drug development. Cancer Invest 23, 264-273.

Perez, E. A. (1999). Current management of metastatic breast cancer. Semin Oncol 26, 1-10.

Peruzzi, F., Prisco, M., Dews, M., Salomoni, P., Grassilli, E., Romano, G., Calabretta, B., and Baserga, R. (1999). Multiple signaling pathways of the insulin-like growth factor 1 receptor in protection from apoptosis. Mol Cell Biol 19, 7203-7215.

Ranger, A. M., Zha, J., Harada, H., Datta, S. R., Danial, N. N., Gilmore, A. P., Kutok, J. L., Le Beau, M. M., Greenberg, M. E., and Korsmeyer, S. J. (2003). Bad-deficient mice develop diffuse large B cell lymphoma. Proc Natl Acad Sci USA 100, 9324-9329.

Roy, S. S., Madesh, M., Davies, E., Antonsson, B., Danial, N., and Hajnoczky, G. (2009). Bad Targets the Permeability Transition Pore Independent of Bax or Bak to Switch between Ca(2+)-Dependent Cell Survival and Death. Mol Cell 33, 377-388.

Royuela, M., Arenas, M. I., Bethencourt, F. R., Sanchez-Chapado, M., Fraile, B., and Paniagua, R. (2001). Immunoexpressions of p21, Rb, mcl-1 and bad gene products in normal, hyperplastic and carcinomatous human prostates. Eur Cytokine Netw 12, 654-663.

Saldanha, A. J. (2004). Java Treeview—extensible visualization of microarray data. Bioinformatics 20, 3246-3248.

Schorr, K., Li, M., Krajewski, S., Reed, J. C., and Furth, P. A. (1999). Bcl-2 gene family and related proteins in mammary gland involution and breast cancer. J Mammary Gland Biol Neoplasia 4, 153-164.

Seo, S. Y., Chen, Y. B., Ivanovska, I., Ranger, A. M., Hong, S. J., Dawson, V. L., Korsmeyer, S. J., Bellows, D. S., Fannjiang, Y., and Hardwick, J. M. (2004). BAD is a pro-survival factor prior to activation of its pro-apoptotic function. J Biol Chem 279, 42240-42249.

Shimamura, A., Ballif, B. A., Richards, S. A., and Blenis, J. (2000). Rsk1 mediates a MEK-MAP kinase cell survival signal. Curr Biol 10, 127-135.

Smith, A. J., Karpova, Y., D'Agostino, R., Jr., Willingham, M., and Kulik, G. (2009). Expression of the Bcl-2 protein BAD promotes prostate cancer growth. PLoS One 4, e6224.

Sunters, A., Fernandez de Mattos, S., Stahl, M., Brosens, J. J., Zoumpoulidou, G., Saunders, C. A., Coffer, P. J., Medema, R. H., Coombes, R. C., and Lam, E. W. (2003). FoxO3a transcriptional regulation of Bim controls apoptosis in paclitaxel-treated breast cancer cell lines. J Biol Chem 278, 49795-49805.

Swanton, C., Marani, M., Pardo, O., Warne, P. H., Kelly, G., Sahai, E., Elustondo, F., Chang, J., Temple, J., Ahmed, A. A., et al. (2007). Regulators of mitotic arrest and ceramide metabolism are determinants of sensitivity to paclitaxel and other chemotherapeutic drugs. Cancer Cell 11, 498-512.

Tan, T. T., Degenhardt, K., Nelson, D. A., Beaudoin, B., Nieves-Neira, W., Bouillet, P., Villunger, A., Adams, J. M., and White, E. (2005). Key roles of BIM-driven apoptosis in epithelial tumors and rational chemotherapy. Cancer Cell 7, 227-238.

Tan, Y., Demeter, M. R., Ruan, H., and Comb, M. J. (2000). BAD Ser-155 phosphorylation regulates BAD/Bcl-XL interaction and cell survival. J Biol Chem 275, 25865-25869.

Upreti, M., Galitovskaya, E. N., Chu, R., Tackett, A. J., Terrano, D. T., Granell, S., and Chambers, T. C. (2008). Identification of the major phosphorylation site in Bcl-xL induced by microtubule inhibitors and analysis of its functional significance. J Biol Chem 283, 35517-35525.

Virdee, K., Parone, P. A., and Tolkovsky, A. M. (2000). Phosphorylation of the pro-apoptotic protein BAD on serine 155, a novel site, contributes to cell survival. Curr Biol 10, 1151-1154.

Weaver, B. A., and Cleveland, D. W. (2005). Decoding the links between mitosis, cancer, and chemotherapy: The mitotic checkpoint, adaptation, and cell death. Cancer Cell 8, 7-12.

Yang, E., Zha, J., Jockel, J., Boise, L. H., Thompson, C. B., and Korsmeyer, S. J. (1995). Bad, a heterodimeric partner for Bcl-XL and Bcl-2, displaces Bax and promotes cell death. Cell 80, 285-291.

Youle, R. J., and Strasser, A. (2008). The BCL-2 protein family: opposing activities that mediate cell death. Nat Rev Mol Cell Biol 9, 47-59.

Yvon, A. M., Wadsworth, P., and Jordan, M. A. (1999). Taxol suppresses dynamics of individual microtubules in living human tumor cells. Mol Biol Cell 10, 947-959.

Zha, J., Harada, H., Osipov, K., Jockel, J., Waksman, G., and Korsmeyer, S. J. (1997). BH3 domain of BAD is required for heterodimerization with BCL-XL and pro-apoptotic activity. J Biol Chem 272, 24101-24104.

Zha, J., Harada, H., Yang, E., Jockel, J., and Korsmeyer, S. J. (1996). Serine phosphorylation of death agonist BAD in response to survival factor results in binding to 14-3-3 not BCL-X(L). Cell 87, 619-628.

Zhou, X. M., Liu, Y., Payne, G., Lutz, R. J., and Chittenden, T. (2000). Growth factors inactivate the cell death promoter BAD by phosphorylation of its BH3 domain on Ser155. J Biol Chem 275, 25046-25051.

All publications, patents and patent applications mentioned in this Specification are indicative of the level of skill those skilled in the art to which this invention pertains and are herein incorporated by reference to the same extent as if each individual publication patent, or patent application was specifically and individually indicated to be incorporated by reference.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

The embodiments of the invention in which an exclusive property or privilege is claimed are defined as follows:

1. A method for increasing the disease-free and/or overall survival of a subject having breast cancer, said method comprising:
    (a) measuring the level of Bad protein in breast cancer cells from said subject using a mouse or rabbit anti-Bad antibody or an antigen binding fragment thereof;
    (b) comparing the level of Bad protein to a level indicative of taxane-sensitivity or taxane-responsiveness;
    (c) classifying said subject, based on the comparison in (b), as being:
        (1) suitable for taxane treatment when a sufficiently elevated level of Bad protein is detected to be indicative of taxane-sensitivity; or
        (2) unsuitable for taxane treatment when a sufficiently low level of Bad protein is detected to be indicative of taxane-resistance; and
    (d) administering a taxane-comprising treatment or a taxane-free treatment to the subject in accordance with the classification in (c) for increasing the disease-free and/or overall survival of said subject.

2. The method of claim 1, wherein the level of Bad protein is measured using: quantitative fluorescence activated cell sorting, enzyme linked immunosorbent assay, immunohistochemistry, quantitative immunohistochemistry, fluorescence resonance energy transfer, Forster resonance energy transfer, immunoblot assay, or co-immunoprecipitation assay.

3. The method of claim 2, wherein the level of Bad protein is measured using immunohistochemistry.

4. The method of claim 1, wherein said measuring is performed using said antigen binding fragment of said mouse or rabbit anti-Bad antibody.

5. The method of claim 1, where said antibody is a monoclonal antibody.

6. The method of claim 1, wherein said taxane is paclitaxel, docetaxel or NAB-paclitaxel.

7. The method of claim 1, wherein the level of Bad protein is measured using a detectable label, wherein the detectable label is: an enzyme, a prosthetic group, a fluorescent label, a luminescent label, a bioluminescent label, a radioactive label, a positron emission tomography label, a paramagnetic metal ion, or any combination thereof.

* * * * *